Figure 1:
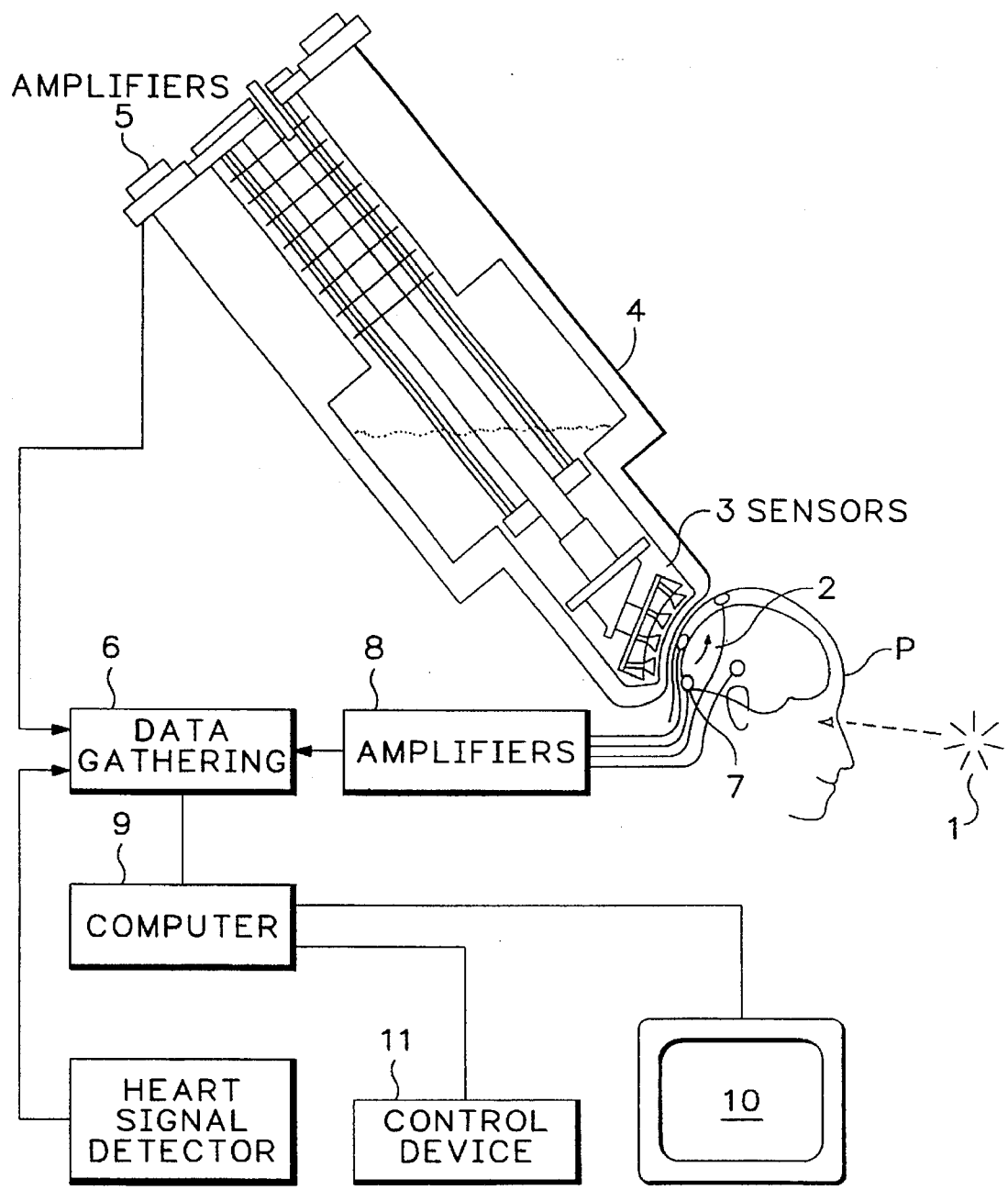

United States Patent [19]
Ilmoniemi

[11] Patent Number: 5,655,534
[45] Date of Patent: Aug. 12, 1997

[54] METHOD AND APPARATUS FOR SEPARATING THE DIFFERENT COMPONENTS OF EVOKED RESPONSE AND SPONTANEOUS ACTIVITY BRAIN SIGNALS AS WELL AS OF SIGNALS MEASURED FROM THE HEART

[76] Inventor: Risto Ilmoniemi, Nuottarinne 4 A 2, 02230 Espoo, Finland

[21] Appl. No.: 446,657

[22] PCT Filed: Nov. 30, 1993

[86] PCT No.: PCT/FI93/00504

§ 371 Date: Jun. 8, 1995

§ 102(e) Date: Jun. 8, 1995

[87] PCT Pub. No.: WO94/12100

PCT Pub. Date: Jun. 9, 1994

[30] Foreign Application Priority Data

Nov. 30, 1992 [FI] Finland .................. 925461

[51] Int. Cl.⁶ ............................................. A61B 5/00
[52] U.S. Cl. .................. 128/653.1; 128/696; 128/731
[58] Field of Search .................. 128/653.1, 696, 128/731, 901; 364/413.05

[56] References Cited

U.S. PATENT DOCUMENTS 5,269,325  12/1993  Robinson et al. ............. 128/653.1

*Primary Examiner*—Ruth S. Smith
*Attorney, Agent, or Firm*—Smith-Hill and Bedell

[57] ABSTRACT

The present invention is related to a method and an apparatus for separating the different components of evoked responses and spontaneous activity of the brain, as well as signals measured from the heart, from each other. The apparatus according to the invention presents the measured signals in graphic form and the user selects from the signals such a time instant, time interval or frequency band, which plausibly can be related to a given source component. The apparatus forms a signal vector from the temporal or frequency signals thus selected, projects the unprocessed signal onto the signal vector thus formed, and subtracts the projection from the unprocessed signals, whereby the projected vector and the set of signals remaining after the subtraction step provide the separation of the unprocessed signals into the selected component and such a part which is clean of contribution of the selected component.

40 Claims, 1 Drawing Sheet

METHOD AND APPARATUS FOR SEPARATING THE DIFFERENT COMPONENTS OF EVOKED RESPONSE AND SPONTANEOUS ACTIVITY BRAIN SIGNALS AS WELL AS OF SIGNALS MEASURED FROM THE HEART

The present invention relates to a method and apparatus for separating the different components of evoked electric and magnetic responses, spontaneous activity of the brain, as well as signals measured from the heart, said components being generated by different sources, said separation of signal components from each other taking place by virtue of subtracting linear combinations of signals obtained from a number of or all measurement channels from the signals obtained from a number of or all measurement channels.

The function of the body can be studied by measuring the electric field E and the magnetic field B. Electric field is ordinarily measured by placing electrodes on the skin and then recording the differential potentials between these. Magnetic field is customarily measured with the help of superconducting SQUID magnetometers. The external measurement of electric brain waves is conventionally called electroencephalography, or EEG; analogously, the measurement of magnetic fields generated by the brain is called MEG, while the measurement of electric potentials resulting from the activity of the heart is called electrocardiography, or ECG, and the measurement of magnetic fields generated by the heart is respectively called magnetocardiography, or MCG [Cf., e.g., J. Nenonen and T. Katila, "Noninvasive Functional Localization by Biomagnetic Methods", J. Clin. Eng. 16, 423–434 and 495–503 (1991)]. In both electrical and magnetic measurements the measurement signal is a weighted sum of the active current flowing in the tissue, herein called the primary current $J^P(r,f)$. If the output signal of a given measurement channel (denoted by the subindex i) is denoted by the symbol $X_i$, the output signal can be expressed:

$$X_i(t) = \int_v L_i(r) \cdot J^P(r,t) dv + n_i(t) \quad (1)$$

where the integration is performed at least over the source volume, that is, the volume of the primary current origin and where the sensitivity function of the measurement channel i for the primary current density at point r is $L_i(r)$. This sensitivity function is ordinarily called the lead field of the measurement channel, because it expresses the weight at which the primary current distribution is coupled to the measurement signal in question. The term $n_i(t)$ in Eq. (1) represents the effect of noise on the output signal of channel i. The signals of the different channels define a time-varying signal vector $$X(t) = (X_1(t), X_2(t), \ldots, X_N(t))^T \quad (2)$$

where N is the number of channels and T denotes transpose. The signal vector can be visualized as a vector of a space whose dimensionality and number of base vectors is equal to the number of measurement channels. Such a space is called the signal space. Typically, the number of measurement channels in the EEG measurements which the present invention relates to is 16–128, in MEG measurement 19–122, and in MCG measurements roughly on the same order of magnitude, while with the evolving techniques, the numbers of channels tend to grow.

Frequently, the primary current distribution intriguing the researcher is composed of a multitude of separate components evolving from primary current densifications at different locations. The term "component" in this context refers to a source whose location and orientation are constant, while its amplitude is time-varying. Such a component has identical time-varying behavior in all measurement channels; however, it is represented in each channel multiplied with a different weight factor depending on the fashion the channel in question is coupled to said source component as expressed in Eq. (1), in other words, depending on the lead field of the channel or sensitivity function $L_i(r)$ at the location of the contributing source. Owing to the temporal coincidence of these components and their weighted summation in the different measurement channels, the measurement results frequently fail to provide sufficient information on the original location of each source, or even on the number and type of components contributing to the measured signals. The impediment arises from the complex summation of several different sources in the different measurement channels according to Eq. (1), thus making it difficult to resolve the contribution of an individual component in the total response.

According to prior art techniques, a multi-component response signal can be resolved through finding by, e.g., iterative methods such a set of elementary primary current source patterns that can interpret the measurement results. A difficulty which frequently arises in the above approach is that the iteration process converges to a local minimum thus giving an incorrect result.

By virtue of the method and apparatus according to the invention, the user selects from the graphical presentation of the multi-channel signal such a time instant, time interval, frequency or frequency band that can plausibly be assumed to represent only one or substantially few signal source components. Given a selected time instant $t_1$, a signal vector $X_s = (X_1(t_1), X_2(t_1), \ldots, X_N(t_1))^T$, later called the template vector, can be formed. Alternatively, given a selected time interval $t_1 \ldots t_2$, a template vector $X_s$, which represents the difference of the signal values at the time instants defining the time interval, can be formed: $X_s = (X_1(t_2) - X_1(t_1), X_2(t_2) - X_2(t_1), \ldots, X_N(t_2) - X_N(t_1))^T$. Further, if a frequency or a frequency band is chosen, the signal is filtered by means of a bandpass filter centered about the chosen spot frequency or tuned to the chosen frequency band, and the template vector is then formed at a time instant of the signal thus filtered, or alternatively, directly from the Fourier transform components of the signal.

The template vector $X_s$ can also be formed from a combination of different frequency and time criteria. For instance, the signals can be first filtered by a bandpass filter and then a time interval is selected over which the signals are averaged to form the template vector $X_s$.

According to Eq. (1), for the selected template vector $X_s$ there is a certain source current distribution $J_s^P(r)$, which generates said vector:

$$X_{s,i} = \int_v L_i(r) \cdot J_s^P(r) dv \quad (3)$$

For the sake of simplicity, the noise term is herein omitted. Ordinarily, $J_s^P(r)$ is not known, but fortunately it need not be known in the method according to the present invention. The essentials are therein that if the amplitude of the current distribution $J_s^P(r)$ changes without causing a change in the form of the current distribution, the corresponding signal vector undergoes a proportional amplitude change without a change in its direction. This fact gives the possibility of employing the projection method according to the invention for separating the source components in the manner described below. It must be noted herein that the projection of vectors and the subtraction of linear combinations from multi-channel signals is conventionally known in the art [Cf., e.g., German patent application Klaus Abraham-Fuchs et al., DE 41 18 126 A1].

The unprocessed signal is projected onto a unit vector parallel to the vector $X_s$, whereby a projected vector $X_p$ is obtained:

$$X_p(t)=(X(t)\cdot X_s/\|X_s\|)(X_s/\|X_s\|)$$

where $\|X_s\|$ is the norm of $X_s$ and $X(t)\cdot X_s=\Sigma_i X_i(t)X_{si}$ is the dot product of $X(t)$ and $X_s$, and $\|X_s\|^2=X_s\cdot X_s$. The projected vector $X_p(t)$ and the remainder $X'(t)=X(t)-X_p(t)$ of the signal now form a decomposition of the unprocessed signal into components of which the latter component $X'(t)$ has no contribution from $J_s^P(r)$ or its amplitude changes. In this manner, the effect of the current pattern eliciting the selected template vector has been filtered away from the unprocessed signal for all time instants, the result being $X'(t)$. Later, the vector $X'(t)$ is also called the filtered signal.

The above-described process can be repeated for $X'(t)$ as many times as is desired by the user, particularly using different time instants, time intervals, frequencies or frequency bands, or combinations thereof, in the formation of new template vectors. Each step achieves the separation of a new, desired component from the signal.

If the measurement signals are recorded at a high noise level, the template vector is corrupted by noise. Consequently, the filtered signal $X'(t)$ is also corrupted through a partial subtraction of such components therefrom that would not have been subtracted in the absence of noise. To alleviate such a disturbing effect, the projected vector $X_p(t)$ (or component) is not completely subtracted from the unprocessed signal but is advantageously weighted in the subtraction step with a factor which is a monotonic function, particularly a monotonically increasing function of the signal-to-noise ratio of $X_p(t)$ prevalent during the determination of the selected template vector $X_s$, in other words, if the signal-to-noise ratio is low thus causing $X_p(t)$ to be highly corrupted by noise, the subtraction is performed by weighting $X_p(t)$ with a factor smaller than one. The weighting factor may be a function of time or frequency.

The embodiment according to the invention facilitates the separation of the different measurement components from each other. Additionally, the number of incorrect measurement results is reduced with respect to the prior art.

In the following the invention is described in greater detail with reference to FIG. 1, which shows diagrammatically an embodiment of the apparatus according to the invention.

With reference to FIG. 1, an apparatus arrangement according to the invention is shown, while the invention is not limited to the applications of such an exemplifying embodiment. A test person P is subjected to a light stimulus 1, which evokes in the brain an electrical activity 2. This activity is measured magnetically by means of SQUID sensors 3, which are placed in a dewar 4 serving as a cooling medium container. The signals of the SQUID sensors are amplified by means of amplifiers 5 and then taken to data gathering equipment 6. The stimulated activity is measured electrically with the help of electrodes 7, the signals are amplified by means of amplifiers 8 and then taken to said data gathering equipment 6. From the data gathering equipment the signals are taken to a data processing unit or a computer 9, which controls a graphic display 10 for presenting the signals to the user. The template vector is selected from disturbance-related or other signal components visible on the graphic display 10 such as, e.g. in brain activity measurement, signal components due to eye movements or due to the electrical activity of the heart. Alternatively, the template vector may be selected on the basis of external disturbances. Thus, on the basis of certain clearly discernible, characteristic property in the displayed signals, employing a control device 11 of said computer such as, e.g., a mouse or keyboard, the user selects a certain time instant, time interval or frequency band on the basis of which the data processing unit then forms a template vector, a corresponding projected signal and a filtered signal. The selection of the frequency band, time interval or time instant may be performed by an algorithm programmed into the computer. The template vector may be chosen from a multi-channel signal measurement at a different time or in a different test.

Without departing from the spirit of the invention, the various details of the invention can be varied and deviated from those of the exemplifying embodiment described above within the scope of the invention as defined in the annexed claims:

1. A method for separating the different components of a measured signal, said different components including evoked electric and magnetic responses, spontaneous activity of the brain and signals measured from the head, said measured signal being obtained from a plurality of measurement channels, said method comprising:

(a) selecting a time instant at which the measured signal is representative of activity of a given source component, (b) forming a template vector from the measured signal at the selected time instant, (c) projecting the input measured signal onto a unit vector parallel to the template vector, whereby for each channel of the measured signal a time-varying projection component of the input measured signal is separated from the measured signal, and (d) subtracting at least part of said projection component from the measured signal.

2. A method according to claim 1, wherein step (a) further comprises selecting a time interval during which the measured signal is representative of activity of a given source component and step (b) comprises forming the template vector from a combination of the measured signal at the selected time instant and changes in the measured signal over the selected time interval.

3. A method according to claim 1, wherein step (a) further comprises selecting a frequency at which the measured signal is representative of activity of a given source component and step (b) comprises forming the template vector from a combination of the measured signal at the selected time instant and frequency components of the measured signal at the selected frequency.

4. A method according to claim 1, wherein step (a) further comprises selecting a frequency band over which the input measured signal is representative of activity of a given source component and step (b) comprises forming the template vector from a combination of the measured signal at the selected time instant and frequency components of the measured signal over the selected frequency band.

5. A method according to claim 1, comprising displaying graphically the measured electrical signal and selecting the time instant on the basis of the graphic display.

6. A method according to claim 1, wherein step (a) comprises using an algorithm programmed into a computer to select said time instant.

7. A method according to claim 1, wherein step (d) comprises subtracting the entire projection component from the measured signal.

8. A method according to claim 1, wherein step (d) comprises subtracting the projection component multiplied by a factor smaller than one from the measured signal, said factor being a monotonically increasing function of signal-to-noise ratio prevalent during the determination of the selected template vector.

9. A method according to claim 8, wherein the factor is a function of time or frequency.

10. A method according to claim 1, further comprising:
(e) selecting a second time instant at which the measured signal is representative of activity of a given source component,
(f) forming a template vector from the measured signal at the time instant selected in step (e),
(g) projecting the measured signal onto a unit vector parallel to the template vector formed in step (f), whereby for each channel of the measured signal a time varying projection component of the measured signal is separated from the measured signal, and
(h) subtracting at least a part of the projection component formed in step (g) from the measured signal.

11. A method for separating the different components of a measured signal, said different components including evoked electric and magnetic responses, spontaneous activity of the brain and signals measured from the heart, said measured signal being obtained from a plurality of measurement channels, said method comprising:
(a) selecting a time interval during which the measured signal is representative of activity of a given source component,
(b) forming a template vector from changes in the measured signal over the selected time interval,
(c) projecting the measured signal onto a unit vector parallel to the template vector, whereby for each channel of the measured signal a time-varying projection component of the measured signal is separated from the measured signal, and
(d) subtracting said projection component from the measured signal.

12. A method according to claim 11, wherein step (a) further comprises selecting a frequency at which the signal is representative of activity of a given source component and step (b) comprises forming the template vector from a combination of changes in the measured signal over the selected time interval and frequency components of the measured signal at the selected frequency.

13. A method according to claim 11, wherein step (a) further comprises selecting a frequency band for which the measured signal is representative of activity of a given source component and step (b) comprises forming the template vector from a combination of changes in the measured signal over the selected time interval and frequency components of the measured signal over the selected frequency band.

14. A method according to claim 11, comprising displaying graphically the measured electrical signal and selecting the time interval on the basis of the graphic display.

15. A method according to claim 11, wherein step (a) comprises using an algorithm programmed into a computer to select said time interval.

16. A method according to claim 11, wherein step (d) comprises subtracting the entire projection component from the measured signal.

17. A method according to claim 11, wherein step (d) comprises subtracting the projection component multiplied by a factor smaller than one from the measured signal, said factor being a monotonically increasing function of signal-to-noise ratio prevalent during the determination of the selected template vector.

18. A method according to claim 17, wherein the factor is a function of time or frequency.

19. A method according to claim 11, further comprising:
(e) selecting a second time interval for which the measured signal is representative of activity of a given source component,
(f) forming a template vector from changes in the measured signal over the time interval selected in step (e),
(g) projecting the measured signal onto a unit vector parallel to the template vector formed in step (f), whereby for each channel of the measured signal a time varying projection component of the measured signal is separated from the measured signal, and
(h) subtracting at least a part of the projection component formed in step (g) from the measured signal.

20. A method for separating the different components of a measured signal, said different components including evoked electric and magnetic responses, spontaneous activity of the brain and signals measured from the heart, said measured signal being obtained from a plurality of measurement channels, said method comprising:
(a) selecting a frequency at which the measured signal is representative of activity of a given source component,
(b) forming a template vector from frequency components of the measured signal at the selected frequency,
(c) projecting the measured signal onto a unit vector parallel to the template vector, whereby for each channel of the measured signal a time-varying projection component of the measured signal is separated from the measured signal, and
(d) subtracting said projection component from the measured signal.

21. A method according to claim 20, wherein step (a) further comprises selecting a frequency band over which the measured signal is representative of activity of a given source component and step (b) comprises forming the template vector from a combination of frequency components of the measured signal at the selected frequency and frequency components of the measured signal over the selected frequency band.

22. A method according to claim 20, wherein step (d) comprises subtracting the entire projection component from the measured signal.

23. A method according to claim 20, wherein step (d) comprises subtracting the projection component multiplied by a factor smaller than one from the input multi-channel signal, said factor being a monotonically increasing function of signal-to-noise ratio prevalent during the determination of the selected template vector.

24. A method according to claim 20, wherein the factor is a function of time or frequency.

25. A method according to claim 20, further comprising:
(e) selecting a second frequency at which the input measured signal is representative of activity of a given source component,
(f) forming a template vector from frequency components of the measured signal at the frequency selected in step (e),
(g) projecting the measured signal onto a unit vector parallel to the template vector formed in step (f), whereby for each channel of the measured signal a time varying projection component of the input multi-channel signal is separated from the measured signal, and (h) subtracting at least a part of the projection component formed in step (g) from the measured signal.

26. A method for separating the different components of a measured signal, said different components including evoked electric and magnetic responses, spontaneous activity of the brain and signals measured from the heart, said measured signal being obtained from a plurality of measurement channels, said method comprising:
(a) selecting a frequency band over which the measured signal is representative of activity of a given source component,
(b) forming a template vector from frequency components of the measured signal over the selected frequency band,
(c) projecting the measured signal onto a unit vector parallel to the template vector, whereby for each channel of the measured signal a time-varying projection component of the measured signal is separated from the measured signal, and
(d) subtracting said projection component from the measured signal.

27. A method according to claim 26, comprising displaying graphically the measured electrical signal and selecting the frequency band on the basis of the graphic display.

28. A method according to claim 26, wherein step (a) comprises using an algorithm programmed into a computer to select said frequency band.

29. A method according to claim 26, wherein step (d) comprises subtracting the entire projection component from the measured signal.

30. A method according to claim 26, wherein step (d) comprises subtracting the projection component multiplied by a factor smaller than one from the measured signal, said factor being a monotonically increasing function of signal-to-noise ratio prevalent during the determination of the selected template vector.

31. A method according to claim 30, wherein the factor is a function of time or frequency.

32. A method according to claim 26, further comprising:
(e) selecting a second frequency band over which the measured signal is representative of activity of a given source component,
(f) forming a template vector from frequency components of the measured signal over the frequency band selected in step (e),
(g) projecting the measured signal onto a unit vector parallel to the template vector formed in step (f), whereby for each channel of the measured signal a time varying projection component of the measured signal is separated from the measured signal, and
(h) subtracting at least a part of the projection component formed in step (g) from the measured signal.

33. Apparatus for separating the different components of a measured signal, said different components including evoked electric and magnetic responses, spontaneous activity of the brain and signals measured from the heart, said measured signal being obtained from a plurality of measurement channels, said apparatus comprising:
a means for selecting a time instant at which the measured signal is representative of activity of a given source component,
a means for forming a template vector from the measured signal at the selected time instant,
a means for projecting the measured signal onto a unit vector parallel to the template vector, whereby for each channel of the measured signal a time-varying projection component of the measured signal is separated from the measured signal, and
a means for subtracting at least part of said projection component from the measured signal.

34. Apparatus according to claim 33, comprising a display means for providing a graphic time-varying display of the projection component and of components of a remainder vector returned by subtraction of the projection component from the measured signal.

35. Apparatus for separating the different components of a measured signal, said different components including evoked electric and magnetic responses, spontaneous activity of the brain and signals measured from the heart, said measured signal being obtained from a plurality of measurement channels, said apparatus comprising:
a means for selecting a time interval during which the measured signal is representative of activity of a given source component,
a means for forming a template vector from changes in the measured signal over the selected time interval,
a means for projecting the measured signal onto a unit vector parallel to the template vector, whereby for each channel of the measured signal a time-varying projection component of the measured signal is separated from the measured signal, and
a means for subtracting said projection component from the measured signal.

36. Apparatus according to claim 35, comprising a display means for providing a graphic time-varying display of the projection component and of components of a remainder vector returned by subtraction of the projection component from the measured signal.

37. Apparatus for separating the different components of a measured signal, said different components including evoked electric and magnetic responses, spontaneous activity of the brain and signals measured from the heart, said measured signal being obtained from a plurality of measurement channels, said apparatus comprising: source component being coupled into a signal component by a sensitivity function, said apparatus comprising:
a means for selecting a frequency at which the measured signal is representative of activity of a given source component,
a means for forming a template vector from frequency components of the measured signal at the selected frequency,
a means for projecting the measured signal onto a unit vector parallel to the template vector, whereby for each channel of the measured signal a time-varying projection component of the measured signal is separated from the measured signal, and
a means for subtracting said projection component from the measured signal.

38. Apparatus according to claim 37, comprising a display means for providing a graphic time-varying display of the projection component and of components of a remainder vector returned by subtraction of the projection component from the measured signal.

39. Apparatus for separating the different components of a measured signal, said different components including evoked electric and magnetic responses, spontaneous activity of the brain and signals measured from the heart, said measured signal being obtained from a plurality of measurement channels, said apparatus comprising:
a means for selecting a frequency band over which the measured signal is representative of activity of a given source component, a means for forming a template vector from frequency components of the measured signal over the selected frequency band, a means for projecting the measured signal onto a unit vector parallel to the template vector, whereby for each channel of the measured signal a time-varying projection component of the measured signal is separated from the input multi-channel signal, and a means for subtracting said projection component from the measured signal.

40. Apparatus according to claim 39, comprising a display means for providing a graphic time-varying display of the projection component and of components of a remainder vector returned by subtraction of the projection component from the measured signal.

* * * * *